United States Patent [19]

Kemp

[11] Patent Number: 5,762,932
[45] Date of Patent: Jun. 9, 1998

[54] COMBINED TREATMENT OF IRON DEPLETION AND IGG ANTIBODY

[75] Inventor: John D. Kemp, Iowa City, Iowa

[73] Assignee: University of Iowa Research Foundation, Iowa City, Iowa

[21] Appl. No.: 718,293

[22] Filed: Sep. 20, 1996

Related U.S. Application Data

[63] Continuation of Ser. No. 358,389, Dec. 19, 1994, abandoned, which is a continuation-in-part of Ser. No. 54,679, Apr. 29, 1993, abandoned, which is a continuation-in-part of Ser. No. 514,706, Apr. 26, 1990, abandoned.

[51] Int. Cl.[6] .................. A61K 39/395; A01N 37/28; A01N 37/18
[52] U.S. Cl. ............... 424/143.1; 424/144.1; 424/155.1; 424/156.1; 514/575; 514/626
[58] Field of Search ............. 424/143.1, 144.1, 424/155.1, 156.1; 514/575, 626

[56] References Cited

U.S. PATENT DOCUMENTS

| | | | |
|---|---|---|---|
| 4,439,196 | 3/1984 | Higuchi | 604/892.1 |
| 4,447,224 | 5/1984 | DeCant, Jr. et al. | 604/67 |
| 4,447,233 | 5/1984 | Mayfield | 604/152 |
| 4,475,196 | 10/1984 | La Zor | 371/29.1 |
| 4,486,194 | 12/1984 | Ferrara | 604/308 |
| 4,487,603 | 12/1984 | Harris | 604/152 |

OTHER PUBLICATIONS

Geran et al. *Cancer Chemother. Reports*, Part 3, vol. 3, No. 2 (1972), pp. 1–85.

Chitambar et al., "Effects of different transferrin forms on transferrin receptor expression . . . " *J. Clin. Invest.* 78: 1538–1546, (Dec. 1986).

Dillman, "Monoclonal antibodies for treating cancer" *Annals of Internal Medicine*, 111:592–603, (1989).

Estrov et al., "In vitro and In vivo effects of deferoxamine in neonatal acute leukemia" *Blood* 69:757, (1987).

Foster et al., *Cancer Treatment Reports* 70:1311–1319, (Nov., 1986).

Hallaway et al., "Modulation of deferoxamine toxicity and clearance by covalent attachment to biocompatible polymers" *Proc. Natl. Acad. Sci. USA*, 86:10108–10112, (1989).

Harris and Emery, "Therapeutic antibodies—the coming of age" *Tibtech*, vol. 11, pp. 42–44, (1993).

Hird and Epenetos, "Immunotherapy with monoclonal antibodies" in *Genes and Cancer*, edited by D. Carney and K. Sikera, John Wiley & Sons, Ltd. Chapter 17, 183–89 (1990).

Huse et al., "Generation of a large combinatorial library of the immunoglobulin repertoire in phage lambda" *Science* 246:1275–1281, (1989).

Kaplinsky et al., "Deferoxamine (Desferal®) induced ocular toxicity" *Ped Hemat Oncol* 5:293, (1988).

Kemp et al., "Role of the transferrin receptor in lymphocyte growth: a rat IgG monoclonal antibody . . ." *J. Immunol.* 138:2422, (1987).

Kemp et al., "Inhibition of lymphocyte activation with anti-transferrin receptor Mabs: a comparison of three reagents . . . " *Cell Immunol.*, 122:218, (1989).

Larrick et al., "In Vitro expansion of human B cells for the production . . . " in *Human Hybridomas and Monoclonal Antibodies* edited by Engleman and Foung, Plenum Press, NY and London, pp. 149–165, (1985).

Lederman et al., "Deferoxamine: a reversible S–phase inhibitor of human lymphocyte proliferation" *Blood*, 64:748, (1984).

Lesley et al., "Inhibition of cell growth by monoclonal anti–transferrin receptor antibodies" *Mol. Cell. Bio.*, 5:1814, (1985).

*Physicians' Desk Reference*, 48 Edition, Desferal®, (1994), pp. 818.

Rao et al., "Effects of alterations in cellular iron on biosynthesis of the transferring receptor in K562 cells" *Mol. Cell. Biol.* 5:595, (1985).

Sauvage et al., "Effects of monoclonal antibodies that block transferrin receptor function on the in vivo growth . . . " *Cancer Res.*, 47:747, (1987).

Sastry et al., "Cloning of the immunological repertoire in *E. coli* for generation of monoclonal catalytic . . . " *Proc. Natl. Acad. Sci.*, 86:5728–4732, (1989).

Schlom, "Monoclonal antibodies: they're more and less than you think" in *Molecular Foundations of Oncology*, edited by Samuel Broder, Williams & Wilkins, Maryland, Chapter 6, pp. 95–134, (1991).

Taetle et al., "Mechanisms of growth inhibition by anti–transferrin receptor monoclonal antibodies" *Cancer Res.*, 46:1759–1763, (Apr., 1986).

Taetle et al., "Combination iron depletion therapy" *J. Natl. Cancer Inst.*, 81:1229, (1989).

Waldmann, "Monoclonal antibodies in diagnosis and therapy" *Science*, vol. 252, pp. 1657–62, (Jun., 1991).

Weissman et al., "Exposure of K562 cells to anti–receptor monoclonal antibody OKT9 results . . . " *Journal of Cell Biology*, 102:951–958, (1986).

Fukuchi et al., "Iron deprivation–induced apoptosis in HL–60 cells" *FEBS Letters 350*, pp. 139–142 (1994).

Hileti et al. "Iron chelators induce apoptosis in proliferation cells," *British Journal of Haematology*, pp. 181–187 (1995).

Kovar et al., "Direct evidence that iron deprivation induces apoptosis in murine lymphoma 38C13" (Submitted for Publication.

Porter et al., "Iron Chelators Promote Apoptosis In Thymocytes and Proliferating Leukaemia Cells" *Lymphocytes and haematology*, p. 114.

Riaz–Ul–Haq et al., "Induction of apoptosis by iron deprivation in human leukemic CCRF–CEM cells" *Experimental Hematology*, 23:428–432 (1995).

Waldmann, "Lymphokine receptors: A target for immunotherapy of lymphomas" *Annals of Oncology*, 5 (Suppl. 1) S13–S17 (1994).

Kemp et al. Blood 76: 991–995, 1990.

Osband et al. Immunology Today 11: 193–195, 1990.

*Primary Examiner*—Toni R. Scheiner
*Assistant Examiner*—Geetha P. Bansal
*Attorney, Agent, or Firm*—Kohn & Associates

[57] ABSTRACT

A method of inhibiting tumor growth includes the steps of depleting intracellular iron levels of tumor cells to increase expression of cellular transferrin receptors in tumor cells and then exposing the tumor cells to monoclonal IgG anti-transferrin receptor antibodies.

1 Claim, 4 Drawing Sheets

COMBINED TREATMENT OF IRON DEPLETION AND IGG ANTIBODY

This is a continuation of Ser. No. 08/358,389 filed on Dec. 19, 1994, now abandoned, which is a CIP of 08/054, 679 filed on Apr. 29, 1993, now abandoned, which is a CIP of 07/514,706 filed on Apr. 26, 1990 now abandoned.

TECHNICAL FIELD

The present invention relates to a novel combination of agents for use in inhibiting tumor growth. More specifically, the invention relates to the combination of an antibody and an agent which depletes intracellular iron and works synergistically to prevent tumor growth and can thereby be broadly applicable in cancer therapy.

BACKGROUND OF THE INVENTION

Iron uptake from exogenous sources is crucial to the growth of normal and neoplastic cells (Lederman et al, 1984). Iron is a necessary component for the maintenance of cellular DNA synthesis. Iron modulates ribonucleotide reductase activity (Lederman et al, 1984). Data from several sources suggest that iron depletion may be a useful strategy in the treatment of neoplasms, particularly those of hematopoietic origin (Estrov et al, 1987; Sauvage et al, 1987; Taetle et al, 1989). Studies in vitro have shown that deferoxamine, an iron chelator, removes iron from ferritin and, to a much less extent, from transferrin. Iron in hemoglobin or cytochromes is not removed by deferoxamine. Deferoxamine was used with some encouraging results in the treatment of a case of acute leukemia (Estrov et al, 1987). Further studies have shown that a monoclonal IgM anti-transferrin receptor antibody had significant efficacy in the treatment of murine lymphoma in vivo (Sauvage et al, 1987). Further, a combination of the iron chelator parabactin and the multivalent IgA anti-transferrin receptor antibody 42/6 was shown to have supra-additive growth inhibitory effects against the HL60 cell line in vitro (Taetle, 1989). The use of an anti-transferrin receptor antibody and iron chelator has been recognized as possibly being an attractive therapeutic strategy because it could potentially allow the utilization of lower doses of a potentially toxic chelator (Kaplinsky et al, 1988). Accordingly, the inventor of the present application has been studying the effects of combination treatment of anti-transferrin receptor antibodies and an iron chelator on the growth of several hematopoietic tumors in vitro.

Taetle et al (1986) disclosed uncertainty about how multivalent IgA and IgM anti-transferrin receptor antibodies actually work. The 1986 paper proposes that receptor degradation and inhibition of receptor internalization by cross-linking both occur but their more recent work emphasizes the significance of surface cross-linking as a dominant mechanism. Unlike this cross-linking mechanism of action of IgA or IgM, Lesley et al (1985) provide evidence that IgG anti-transferrin antibodies cause receptor down-regulation by themselves, but do not inhibit tumor growth unless further cross-linked by anti-immunoglobulin antibodies. Their paper discloses that IgM antibodies appear to cross-link when receptor density is high enough and cause growth inhibition. Thus, Lesley et al (1985) postulate that extensive cross-linking is required for significant growth inhibition of tumor cells.

While both Taetle et al (1986) and Lesley et al (1985) do not dispute the concept that IgG anti-transferrin receptor antibodies cause enhanced receptor internalization and degradation, they do suggest that IgG anti-transferrin antibodies are poor growth inhibitors.

Weissman et al (1986) provide further evidence that IgG anti-transferrin receptor antibodies cause down-modulation and degradation. Growth inhibition is not addressed in the Weissman et al paper.

Researchers have utilized combined multivalent IgA or IgM anti-transferrin receptor antibodies in combination with iron chelators. However, even though IgA, IgM and IgG are all antibodies, it was expected that IgG would be ineffective in a combination therapy with iron chelator to inhibit tumor growth. This conclusion was drawn from the evidence showing that IgG cannot extensively cross-link surface receptors. Unexpectedly, the inventors of the present invention have found significant synergism in the effects of combination treatment with anti-transferrin receptor IgG antibodies and depletors of intracellular iron on the growth of tumors.

Unlike methods utilizing antibodies which extensively cross-link surface receptors, it is proposed that the IgG anti-transferrin receptor antibodies cause receptor down modulation and are almost as potent an inhibitor as multivalent IgM anti-transferrin receptor antibodies while potentially providing further clinical significance.

SUMMARY OF THE INVENTION

In accordance with the present invention there is provided a method of inhibiting tumor growth by depleting intracellular iron levels of tumor cells to increase expression of cellular transferrin receptor in the tumor cells and exposing the tumor cells to monoclonal IgG anti-transferrin receptor antibody.

FIGURES IN THE DRAWINGS

Other advantages of the present invention will be readily appreciated as the same becomes better understood by reference to the following detailed description when considered in connection with the accompanying drawings wherein:

FIGS. 1A–1E show the effect of combined treatment with deferoxamine (DFO) and the IgG anti-transferrin receptor antibody (ATRA) C2F2 on tumor cell growth. Five lymphoid tumors, 69J (FIG. 1A), NFS-1 (FIG. 1B), 70Z (FIG. 1C), EL4 (FIG. 1D), and BAL8 (FIG. 1E), respectively were cultured with increasing dosed of DFO, with open circles) or without (closed circles) the presence of ATRA at 25 ug/ml, as described in the Materials and Methods portion of the Experimental Findings Section of the present application. The decreases in thymidine incorporation were closely related to decreases in viable cell yields in three experiments (not shown). The control levels of incorporation were 217, 126 cpm (69J), 546,036 cpm (NFS), 491,648 cpm (70Z), 490,190 cpm (EL4), and 428,943 cpm (Bal8). Normal rat IgG at 25 ug/ml had no significant effect at several concentrations of DFO with each tumor. Very similar results were obtained in a repetition of the same protocol and have also been repeatedly observed for each of the five tumors in subsequent related experiments.

FIG. 2 shows two-way dose/response analysis of the effects of DFO and an IgG ATRA on growth of the EL4 tumor. Cells were cultured as noted in Materials and Methods and were exposed to varying concentrations of the ATRA for each of the noted doses of DFO. Percent inhibition of thymidine incorporation was determined from a tumor alone control of 456,992 cpm. Arrows denote half-maximal inhibition points for each curve. Very similar results were obtained in a repetition of the same protocol.

FIG. 3A shows flow cytometric analysis of the effects of DFO and an IgG ATRA on surface expression of the transferrin receptor of NFS cells. Cells were cultured for 48 hours as noted in Materials and Methods and were exposed to DFO, the IgG ATRA, or a combination of the two. Curve 1 represents data obtained from cells in the presence of normal rat IgG while curve 2 represents cells exposed to the IgG ATRA (both reagents at 25 ug/ml).

FIG. 3B shows curve 1 represents cells exposed to DFO alone (5ug/ml) while curve 2 representing cells exposed to DFO and the ATRA (5 and 25 ug/ml, respectively). In the same experiment, lower doses of DFO alone produced smaller increases in surface expression of the transferrin receptor, while higher doses produced only slightly higher increases; the combination of DFO/ATRA produced receptor down-modulation at all doses of DFO (not shown). Very similar data were obtained in two repetitions of the same protocol with the NFS tumor, and related studies have shown that the other four tumors also show receptor down-modulation when treated with DFO and the IgG ATRA.

FIG. 4 shows a comparison of the enhancement of inhibition produced by an IgG ATRA to that produced by an IgM ATRA, when both are used in combination with DFO. EL4 cells were cultured as noted in Materials and Methods. The curved marked by closed circles represents the effect of DFO alone; that marked by open circles represents the effect of DFO and the IgG ATRA C2F2; and that marked by closed triangles represents the effect of DFO and the IgM ATRA R17-208. Both ATRAs were used at a concentration of 25 ug/ml. Very similar data were obtained in a repetition of the same protocol.

FIGS. 5A–5D represent a series of four graphs showing the results of experiments wherein mice in Group A (FIG. 5A) were untreated, each mouse being followed individually, mice in Group B (FIG. 5B) were treated HES—DFO alone, in Group C mice (FIG. 5C) were treated IgG ATRAs only, and in Group D (FIG. 5D), mice were treated IgG ATRAs+HES–DFO.

DETAILED DESCRIPTION OF THE INVENTION

Figure 1A:
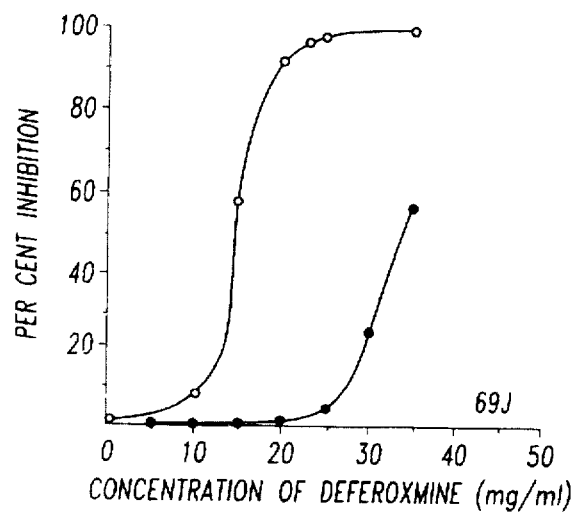
Figure 1B:
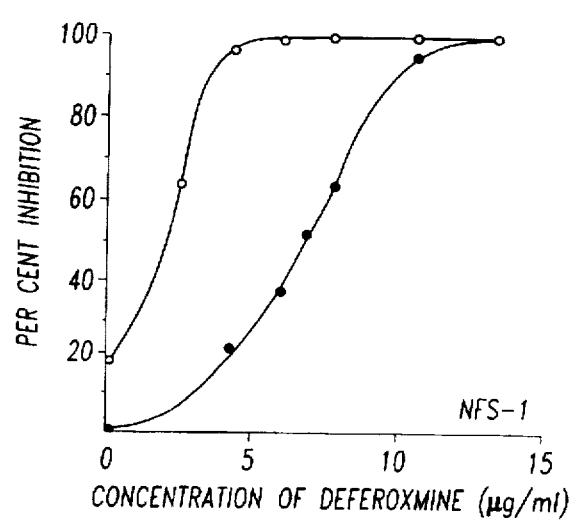
Figure 1C:
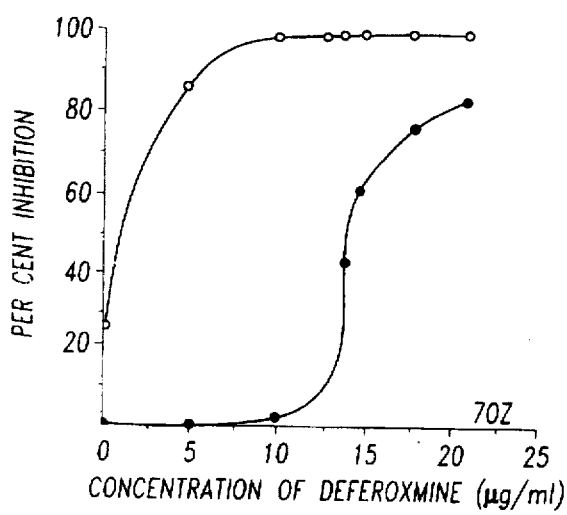
Figure 1D:
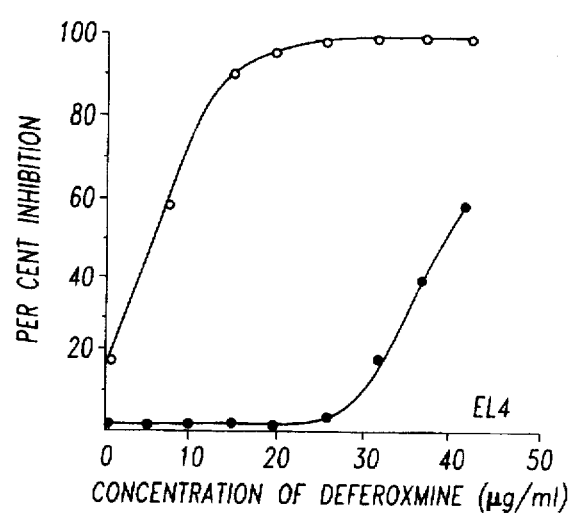
Figure 1E:
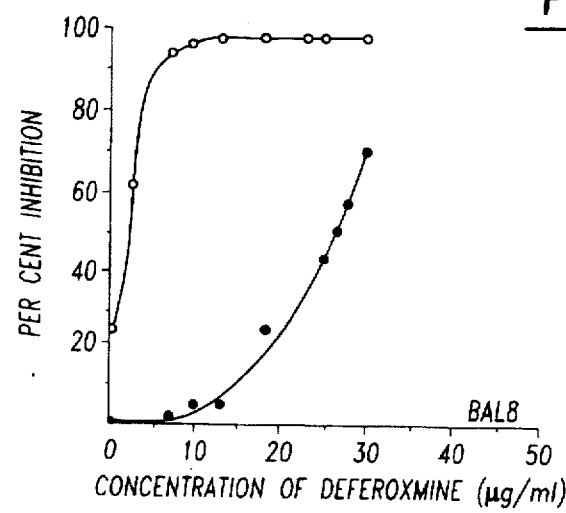

The present invention presents a combination of agents for inhibiting tumor growth by depleting intracellular iron levels of tumor cells and then exposing the cells to monoclonal IgG anti-transferrin receptor antibody. The depletion of intracellular iron levels of the tumor cells increases expression of cellular transferrin receptors in the tumor cells, as detailed in the many papers cited in the background section.

Cells can be depleted of intracellular iron by several methods, such as exposing the cells to an iron chelator, such as deferoxamine (DFO), deferoxamine chemically coupled to hydroxyethyl starch (the bound combination is known as either HES-DFO or as HMW–DFO for high molecular weight deferoxamine and is available from Biomedical Frontiers of Minnesota) and parabactin. The coupling or covalent attachment of deferoxamine to a biocompatible polymer such as hydroxyethyl starch is disclosed by Hallaway et al (1989). DFO, as an exemplary iron chelator, is available as deferoxamine mesylate. (Desferal® is a trademark for deferoxamine mesylate USP, manufactured by CIBA) It has been used clinically in acute iron poisoning. (see Physicians'Desk Reference, 1994, page 818 for dosage and administration.) However, deferoxamine mesylate has a very short plasma half–life while that of HES–DFO is much longer. HES–DFO is also less toxic than deferoxamine mesylate for a given molar quantity of DFO as disclosed by Hallaway et al. (1989).

Alternatively, cellular iron levels can be depleted by the exposure of the cells to gallium, as in the form of transferrin-gallium. Chitambar et al. (1986) and Foster et al. (1986) disclose the anti-tumor activity of gallium. The Chitambar et al (1986) paper suggests that transferrin-gallium impairs intercellular release of 59Fe from transferrin by interfering with the process responsible for intracellular acidification. Accordingly, transferrin-gallium and possibly other gallium compounds may be suitable for use with the present invention.

Once the tumor cells are partially depleted of intracellular iron, the expression of cellular transferrin receptor in the cells is increased. The tumor cells are then exposed to monoclonal IgG ATRAs. IgG ATRAs can be biologically derived by methods well known in the art. Alternatively, equivalents of IgG ATRA which are genetically engineered can be used in accordance with the present invention. Examples of genetically engineered equivalents of IgG are disclosed by Sastry et al (1989) and Huse et al. (1989). Guidance for the use of therapeutic monoclonal antibodies is provided by Harris and Emery (1993), Waldmann (1991), Dillman (1989), Larrick et al (1985), Schlom (1991) and Hird and Epenetos (1990).

In the method of the present invention, the combination of agents for inhibiting tumor growth by depleting intracellular iron levels of tumor cells and then exposing the cells to monoclonal IgG anti-transferrin receptor antibody can be administered in various ways and can be administered alone or in combination with pharmaceutically acceptable carriers. According to the present invention, however, any vehicle, diluent, or additive used would have to be compatible with the agent for depleting intracellular iron levels and the monoclonal antibody. The patient being treated is a warm-blooded animal and, in particular, mammals including man.

The combination of agents is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art. The amount must be effective to achieve improvement including, but not limited to, reduced tumor mass and improved survival rate or other measures that are selected as appropriate measures by those skilled in the art.

It is noted that humans are treated generally longer than the mice exemplified herein which treatment has a length proportional to the length of the disease process and drug effectiveness. The doses may be single doses or multiple doses or continuous infusion over a period of several days.

A pharmacological formulation of the present invention can be administered to the patient in an injectable formulation containing any compatible carrier, such as various vehicle, adjuvants, additives, and diluents; or the compounds utilized in the present invention can be administered via intravenous infusion or parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several hours to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

In the preferred embodiment, a slow intravenous infusion of several hours is used with a delivery of from 100 to 500 mg/M$^2$.

The following data support the contention that the combination of the iron depletion resulting in increased transferrin receptor expression with the effect of the IgG antibody to cause transferrin receptor down modulation and degradation results in the significant synergistic effect of the combined therapy to inhibit tumor growth.

Although the data below have been compiled for hematopoietic cells, it is very likely that the present combination therapy would also be effective in solid tumors, possibly to a greater extent than combined therapy using IgM or IgA with iron chelators. This is because the IgG antibody diffuses into interstitial fluids much more freely than IgM or IgA antibodies and IgG antibodies are therefore much more likely to be able to affect tumor cells outside of the vascular spaces.

The following data illustrate the effects of the combination treatment with monoclonal IgG anti-transferrin receptor antibodies and an iron chelator on the growth of several hematopoietic tumors both in vitro and in vivo. The data characterize quantitatively and mechanistically the effects of the combined therapy.

The following Examples further demonstrate the in vitro and in vivo utility of the present invention. The present invention can serve as a diagnostic test for screening tumor types and individual tumors for susceptibility to iron depletion as demonstrated in the in vitro studies herein below.

The present invention can also be used to control the growth of cultured tumor cells as is demonstrated in the in vitro studies. Tumor-associated factors and various growth factors are harvested from tumor cells grown in culture and used as reagents for cell culture and in biological assays. The present invention provides a method of controlling the growth of the tumor cells in vitro and therefore modulates the production of these factors from tumor cells. In general, there is an optimum cell growth rate - cell density that provides the highest cell/product yield. As shown in Examples 1 and 3 hereinbelow the dose of DFO and ATRA can be scaled to establish the amount of control and/or inhibition needed.

In addition, tumor cell cultures can serve as test systems for various biologicals and as such the providing of such cells and the ability to control growth rate as well as provide a standard measure of inhibition is provided by the present invention. The following in vitro results demonstrate the capability of in vitro effects of the present invention.

The full set of Examples show that combined treatment in accordance with the present invention was efficacious in vivo in stopping the initial outgrowth of tumors. The further evidence demonstrates that tumors which have been allowed to become established and which are therefore more difficult to treat, undergo significantly more frequent regression when exposed to combined treatment with DFO and a pair of IgG ATRAs than when exposed to pair of IgG ATRAs alone. Hence, the present invention finds utility in both in vitro and in vivo applications.

The above discussion provides a factual basis for the use of depleting intracellular iron levels of tumor cells and exposing the tumor cells to monoclonal IgG anti-transferrin receptor antibody. The methods used with and the utility of the present invention can be shown by the following examples.

EXPERIMENTAL FINDINGS

EXAMPLE 1

IN VITRO STUDIES

Materials and Methods

Lymphoid tumors: The B-cell tumors 702, NFS-1, and 69J were obtained from Drs. Bryan Van Ness (now at the University of Minnesota), Herbert Morse (NIH), and Richard Lynch (University of Iowa), respectively. The T-cell tumors Bal8 and EL4 were also obtained from Dr. Lynch. Each has been maintained in the laboratory of the inventor for several years.

Deferoxamine: The bacterial iron siderphore deferoxamine (produced under the name Desferal® by Ciba-Geigy Inc., Sumitt, N.J.) was obtained from the Pharmacy of the University of Iowa Hospitals and Clinics. A fresh vial containing 500 mg of lyophilized deferoxamine was used for each experiment and was resuspended with distilled water to a 100mg/ml stock solution before dilution in tissue culture media.

Anti-transferrin receptor antibodies (ATRAs): The details of the derivation of the IgG2a rat anti-mouse transferrin receptor antibody C2F2 have been previously published (Kemp et al, 1987). C2F2 and the IgM ATRA R17-208, obtained from the American Type Culture Collection (ATCC) (TIB 220), were purified as previously described (Kemp et al, 1989). Culture conditions: For all of the experiments, each of the tumors were cultured with a starting density of 1.25×105 cells/ml. The tissue culture media consisted of RPMI-1640 supplemented with 10% FCS, 0.1 mM nonessential amino acids, 1.0 mM sodium pyruvate, 2.0 mM L-glutamine, 100 U/ml penicillin, 100 ug/ml streptomycin, 10 mM hepes, and 5×10-3M 2ME. The cultures that were assayed for thymidine incorporation were carried out in triplicate in 200 ul volumes in 96 well flat-bottom plates (Corning or Costar), and were harvested for scintillation counting after a pulse with 1 uC/well of [3H] thymidine (Amersham, Arlington Heights, Ill) during the last four or six hours of a standard 48-hour culture period. Standard deviations of triplicate cpm data were, with rare exceptions, less than 5% of group means. Cultures that were harvested for FACS analysis were carried out in T-25 or T-75 flasks.

Flow cytometric analysis: Cells harvested from culture were stained with C2F2 and a fluorescein conjugated F(ab')2 preparation of mouse anti-rat IgG (Jackson Immunoresearch, West Grove, Pa.). In those cases where C2F2 was included in the culture, applicants (and others) have shown that most of the transferrin receptors are already bound by the ATRA and this can be detected by the addition of the secondary reagent only. Nevertheless, a small additional increment in staining intensity is routinely observed when a post-culture exposure to the ATRA is included, and this has become the applicant's standard practice (Kemp et al. 1989). The analysis was carried out on a FACS 440 (Becton-Dickinson) equipped with four decade logarithmic signal amplifiers. Data were processed and plotted with the Electric Desk software run on a Dec Vax 750 computer.

IN VITRO RESULTS—DEFEROXAMINE

Each tumor to be tested was evaluated beforehand with respect to its sensitivity to deferoxamine.

The data in FIG. 1 show that the inhibition of thymidine incorporation produced by submaximal concentrations of DFO is dramatically enhanced in the presence of the IgG ATRA for each of the five tumors tested. The ATRA alone, even at the relatively high concentration of 25 ug/ml, produces only modest inhibition—ranging from 0 to 26% depending upon the tumor in question. That IgG ATRAs, by themselves, are poor inhibitors of tumor cell growth in vitro is entirely consistent with prior studies by others (Lesley et al, 1985; Taetle et al, 1986).

Although at certain doses of DFO the effect of the reagents combined produces very impressive synergistic inhibition, a more conservative way to gauge the interaction of the two reagents is to compare the estimated dose of DFO required to produce half-maximal inhibition in the presence of the ATRA versus that required in the absence of the ATRA, to establish an index of enhancement by dividing the latter number by the former. The numerator, in all cases, takes into account the baseline inhibition caused by the ATRA itself. The indices thereby obtained for each tumor are 2.5 (69J), 2.5 (NFS), 4.0 (70Z), 5.3 (EL4), and 8.8 (Bal8), for the experiment shown. A second experiment yielded indices of 2.0 (69J), 2.5 (NFS), 3.0 (70Z), 4.0 (EL4), and 5.0 (Bal8); subsequent related experiments have further confirmed these observations. It appears that all of the tumors tested show a reproducible synergistic enhancement of inhibition when the two agents are used in combination, and that certain tumors reproducibly show more enhancement than others.

Figure 2:
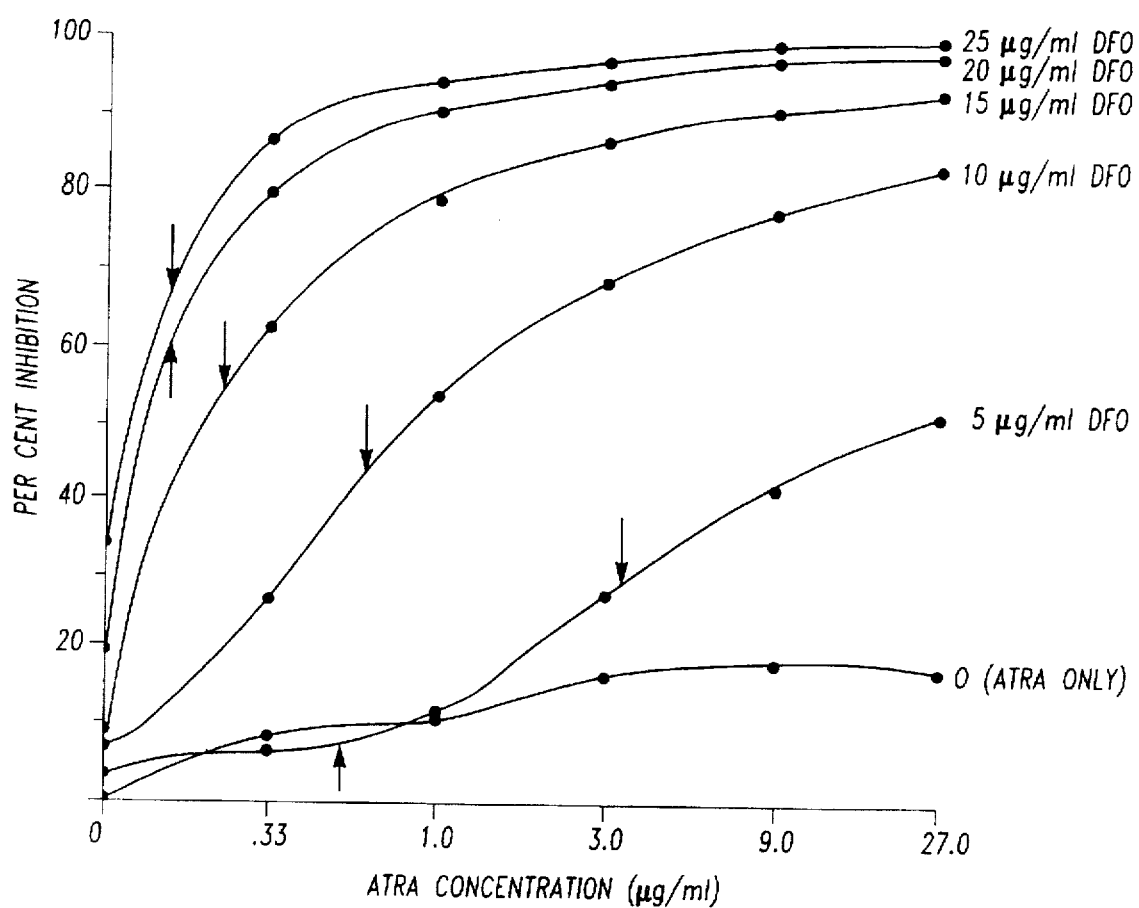

The dose range of the ATRA required to produce synergistic inhibition was determined. The data are presented in FIG. 2. At the very lowest dose of DFO employed (5 ug/ml), the amount of ATRA required to produce half-maximal inhibition is greater than that required in the absence of DFO. This result would be expected from a simple increase in target antigen density if all other factors remained unchanged. However, with each subsequent increase in the does of DFO the amount of ATRA required to produce half-maximal inhibition declines to an apparent minimum of about 100 to 200 ng/ml. The latter observation suggests that as the dose of DFO increases, so does the inhibitory efficiency of the ATRA.

The mechanisms involved in IgG ATRA/DFO synergism were characterized. Flow cytometric studies were conducted of changes in surface expression of the transferrin receptor resulting from the treatments under study.

Figure 3A:
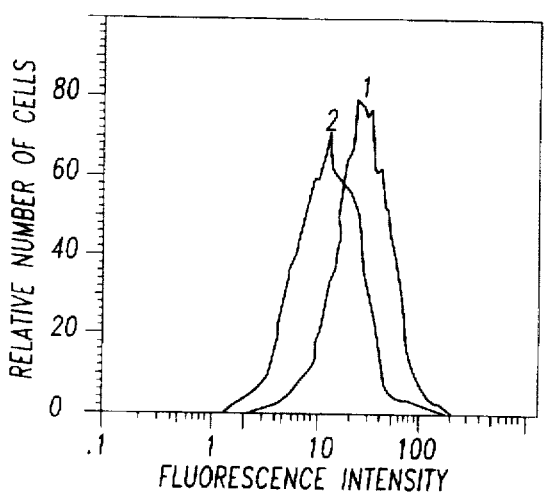
Figure 3B:
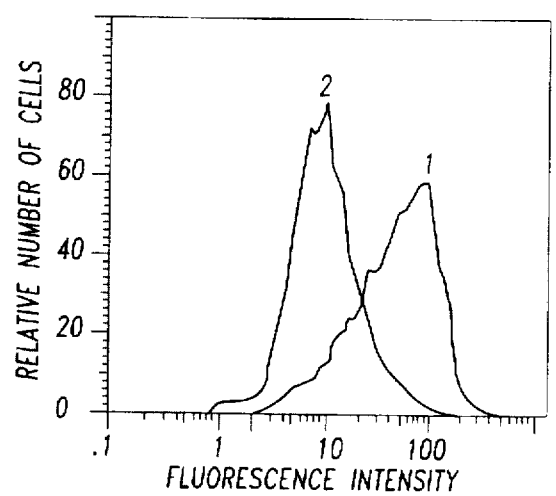

The data represented in panel A of FIG. 3 show that the IgG ATRA alone causes about a three-fold drop in surface receptor expression when compared to the control. This result was expected from prior work (Lesley et al, 1985; Weissman et al, 1986). The data represented in panel B of FIG. 3 show that DFO alone causes a three-fold increase in surface receptor expression (compare curve 1 in panel B to curve 1 in panel A). This result was also expected from prior work (Rao et al, 1985). Curve 2 in panel B shows the effect of the reagent combination. It is clear that ATRA-induced receptor down-modulation persists and dominates in spite of the presence of a stimulus for enhanced receptor expression.

Figure 4:
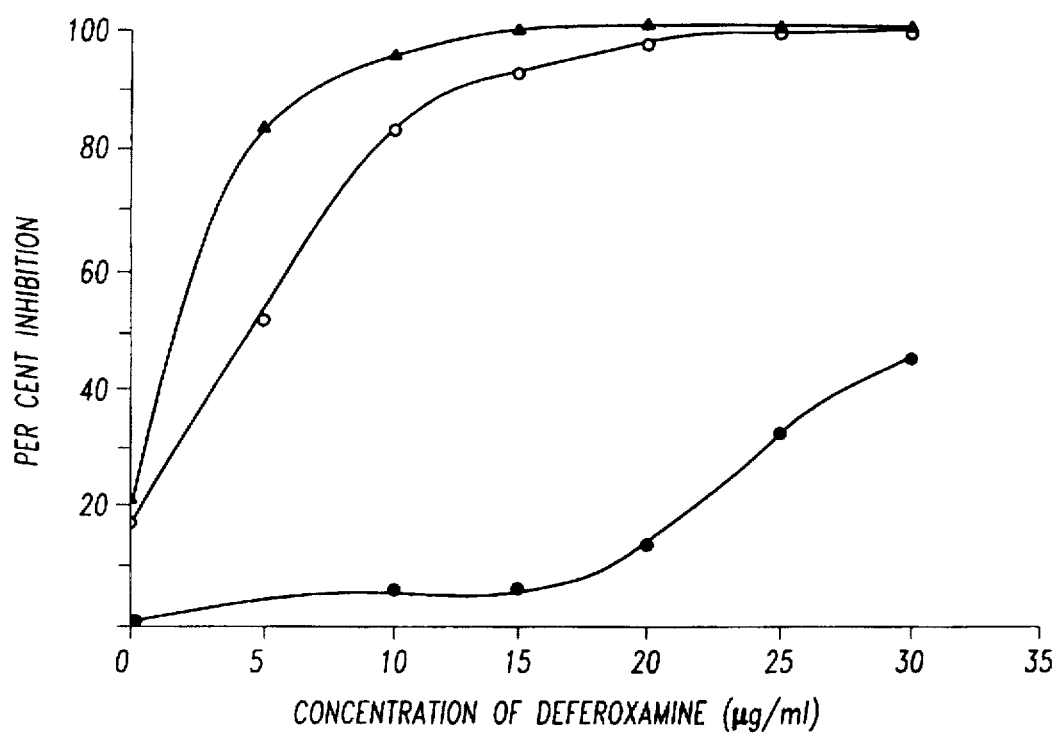
Figure 5A:
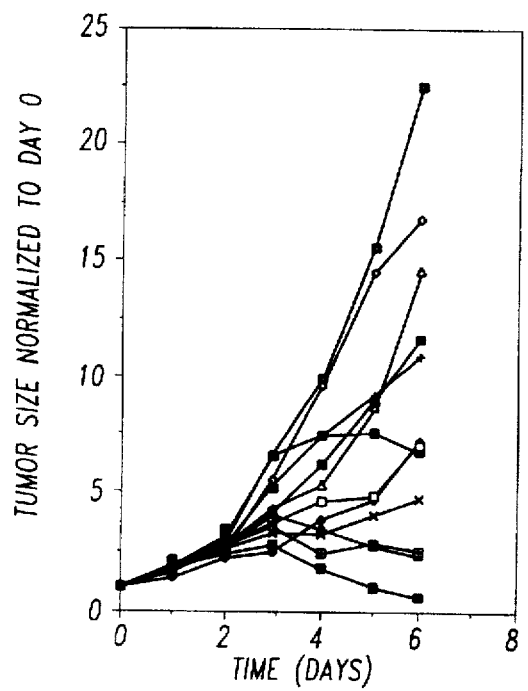
Figure 5B:
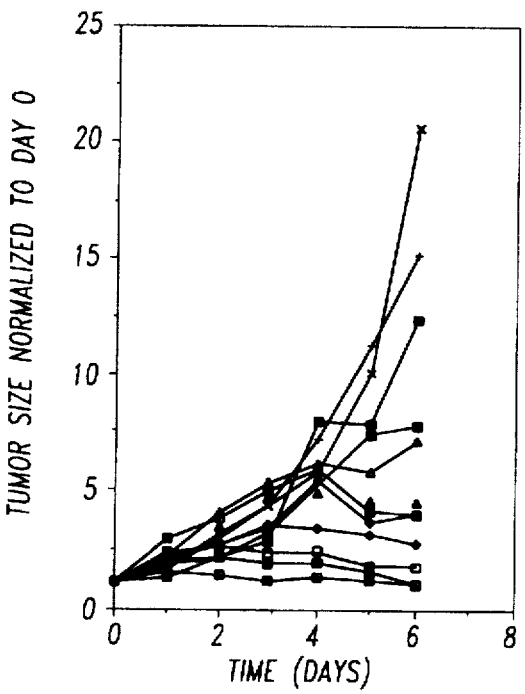
Figure 5C:
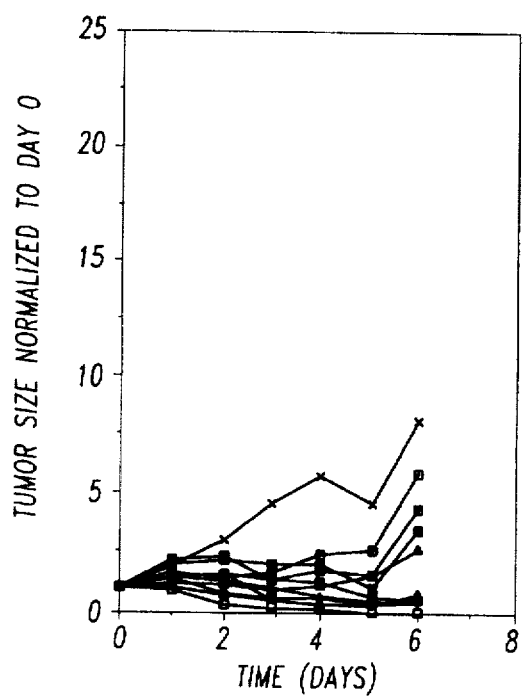
Figure 5D:
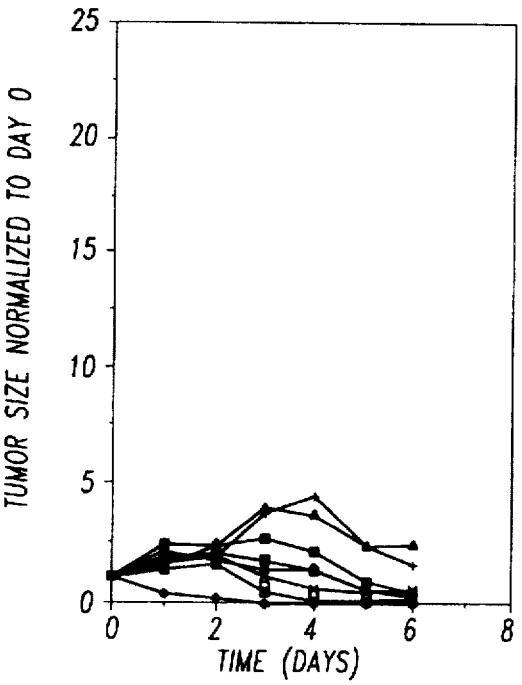

It has generally been observed that IgG ATRAs, as single agents, are poor inhibitors of tumor cell growth and the data presented here continue to support that view. Therefore, having made the unexpected observation that an IgG ATRA can cause synergistic growth inhibition when used with an iron chelator, growth inhibition was compared with that produced by an IgM ATRA in combination with DFO. For the comparison, an IgM ATRA was chosen that has recently been shown to have anti-tumor effects in vivo (Sauvage et al, 1987). The data presented in FIG. 4 show that the IgM ATRA is only modestly more effective than the IgG ATRA in that 99% inhibition of thymidine incorporation occurs at a slightly lower concentration of DFO. Nevertheless, both ATRAs produce 99% inhibition at concentrations of DFO that would otherwise have only very modest effects. The relative inhibitory potencies of the IgM and IgG ATRAs in these experiments are quite similar to those seen in normal lymphocyte activation protocols (Kemp et al, 1989).

The above data confirm and significantly extend the work recently reported by Taetle et al, (1989). Taetle et al (1989) reported superadditive inhibition of HL60 growth in vitro when that tumor was exposed to a combination of an iron chelator parabactin and the multivalent IgA ATRA 42/6. The present invention provides an advancement by showing that synergistic inhibition of tumor growth also occurs. In all cases tested, 5 murine lymphoid tumors are exposed to deferoxamine and the monoclonal IgG anti-transferrin receptor C2F2 in vitro. The results were unexpected because while it has been shown that monoclonal IgG anti-transferrin receptor antibodies can act as potent inhibitors of normal lymphocyte activation, such reagents have nonetheless consistently failed to produce significant inhibition of tumor cell growth when used alone (Kemp et al, 1989; Lesley et al, 1985; and Taetle et al, 1989).

The above data provide further support for the generally accepted view that monoclonal IgG anti-transferrin receptor antibodies impair cell function by causing down-modulation and degradation of the transferrin receptor, thereby impairing the delivery of iron. This occurs even when surface receptor density is increased by treatment with the deferoxamine. Moreover, the antibody dose response curve converts into a pattern that shows a progressive shift to the left, rather than continuing the shift to the right with increasing doses of deferoxamine. This indicates that the antibody actually becomes a more efficient inhibitor.

EXAMPLE 2

IN VIVO STUDIES

Materials and Methods

To demonstrate the in vivo utility of the invention, four groups of C3H/HEJ mice were injected intradermally with 50,000 cells of histocompatible 38C13 B-cell lymphoma and observed for 11 days. One experimental Group (A) received deferoxamine only. This group received the deferoxamine by subcutaneous infusion pump and intramuscular injection. A second Group (B) was given saline via infusion pumps. A third Group (C) was given injections of monoclonal anti-transferrin receptor antibody C2F2 without deferoxamine. Finally, the fourth Group (D) received combined treatment with DFO and the monoclonal anti-transferrin receptor antibody.

Tumor weight, in milligrams, was measured and estimated by a previously reported technique (*Cancer Chemother. Rep.*, Part 3, 3:18–55, 1972).

IN VIVO RESULTS

The tumor weights measured and estimated as described above were as follows:

Group A: 1,761±68(±1 S.D.)

Group B: 1,396±722

Group C: 342±128

Group D: 172±45

Groups A and B are not significantly different by t-test, thus indicating that DFO treatment alone had no effect on tumor growth. Group C is significantly different from either Group A or Group B at the 0.001 level, thus indicating that treatment with the IgG anti-transferrin receptor antibody inhibited tumor growth. Finally, Group D is significantly different from Group C at the 0.05 level, thus indicating that combined treatment with DFO and the monoclonal antibody provided yet a further reduction in tumor growth. The latter result indicates synergy because DFO alone had no detectable effect.

In a second related experiment, the combined treatment group (equivalent to Group D in the first experiment) included two mice which showed no detectable tumor growth at all. Moreover, an additional control group for the injection of the monoclonal antibody consisting of injection of an equal concentration of normal rat IgG showed no inhibition of tumor growth. This was the expected result and provides a strong indication that the anti-transferrin receptor antibody effect is specific.

These experiments demonstrate the in vivo utility of the findings previously obtained in vitro (Kemp et al, 1990). Moreover, they are more rigorous and relevant to potential human therapy because the artificial nude mouse/human tumor xenograph model has not been employed. In this experiment, a normal mouse served as host for a mouse tumor and was treated with an anti-mouse transferrin receptor antibody. Thus, normal tissue expression of the transferrin receptor is taken into account with respect to the possibility that normal tissue might bind antibody and make it less effective for tumor therapy.

The antibody has been effective and it has interacted with DFO, as expected from the in vitro studies. This is unambiguous evidence of in vivo utility of the concept put forth based on the in vitro studies.

Further, the monoclonal anti-transferrin receptor antibody has been given to humans in Phase I trials with no adverse effects in doses up to 300 mg/M$^2$.

EXAMPLE 3

USE OF HMW-DFO IN VIVO

Materials and Methods

The experiments were conducted in nearly identical manner to the in vivo studies with deferoxamine previously discussed above in Example 2. That is, 50,000 cells of 38C13 lymphoma were given intradermally to C3H mice in all groups.

As in the Deferoxamine experiments, the IgG ATRA was administered in 3 mg. doses on days 0, 3, 6, and 9. The experiments were terminated on day 11. HMW-DFO was given as a single daily intraperitoneal injection of 0.5 ml. of a 26mM solution. The starch control was administered in a similar manner (0.5 ml i.p. of a 10% solution daily). An additional control in the second experiment (not shown) utilized normal rat IgG in the same concentrations and dose schedule as C2 and the result was not significantly different than the untreated group (ATW of 0.44g-96% of control).

RESULTS—HMW-DFO

The treatment groups and results were as follows:

| GRP Rx | AVG TUM WGT (EXP1) | % CON | AVG TUM WGT (EXP2) | % CON |
|---|---|---|---|---|
| 1. Untr. Con | .57 g | 100% | .46 g | 100% |
| 2. HMW-DFO | .69 g | 121% | .59 g | 128% |
| 3. Starch Con. | .69 g | 121% | .55 g | 120% |
| 4. HMW + C2 | .00 g | 0.0% | .00 g | 0.0% |
| 5. C2 Only | .33 g | 58% | .09 g | 20% |
| 6. Starch + C2 | .48 g | 84% | .26 g | 57% |

EFFECTS ON TUMOR GROWTH: HMW-DFO, IGG ATRA, OR BOTH

All percent values are relative to the untreated control group. There is a slight enhancement in tumor growth in groups 1 and 2 that may be due to the starch polymer. The interaction between HMW-DFO and the ATRA can clearly be called synergistic in both experiments since the HMW-DFO has no inhibitory effect by itself. There is complete inhibition of tumor growth in all animals receiving HMW-DFO and the IgG ATRA in both experiments. There is no apparent toxicity. This is further unambiguous evidence of the in vivo utility of the concept put forth.

It is believed that the capacity to cause inhibition of tumor cell growth when used in combination with a depletor of intracellular iron will be a feature common to most, if not all, IgG anti-transferrin receptor antibodies. Preliminary comparative studies have been conducted with two other IgG anti-transferrin rat antibodies to date and both show synergy with deferoxamine. The mouse anti-human transferrin receptor antibody OKT9 has shown synergy against HL60 and the rat anti-mouse transferrin receptor YE1 has shown synergy against EL4. This apparent similarity between IgG anti-transferrin receptor with respect to their synergy with deferoxamine is similar to their demonstrable similarity in other functional assays. Prior studies that were performed by the inventor of the present invention indicated that three IgG anti-transferrin receptors antibodies exhibit similar profiles of inhibitory capacities in a variety of normal lymphocyte activation protocols (Kemp et al, 1989). The same prior studies showed, in addition, that an IgM anti-transferrin receptor antibody had only a modest advantage as in an inhibitor in vitro. This prior data is consistent with the data presented herein. From a therapeutic point of view, the latter finding has real potential significance because IgG antibodies diffuse into interstitial fluids much more freely than IgM or IgA antibodies. Accordingly, IgG antibodies are more likely to be able to affect tumor cells outside of vascular spaces.

EXAMPLE 4

TREATMENT OF ESTABLISHED TUMORS

A 38C13 lymphoma was allowed to become established intradermally in C3H mice for seven days prior to the beginning of the following treatments. In Group A, mice were untreated and followed individually. In Group B, mice were treated with HES-DFO alone. In Group C, IgG ATRAs only were given to mice. In Group D, mice were IgG ATRAs and HES-DFO. Treatment consisted of either HES-DFO alone (0.5 mL of 26 µM solution given intraperitoneally on a daily basis) as in previous experiments described above. IgG ATRAs were given alone (1.5 mg each of the rat antimouse IgG ATRAs C2 and RL34 given intraperitoneally on treatment days 1 and 4). The combination of the two forms of treatment were provided to Group D in a similar dose regiment.

As in the experiments described above, controls such as HES alone or normal rat IgG have no significant effect on tumor growth.

FIG. 5 shows the results obtained in key experimental groups. In Group A, the untreated mice, each mouse was followed individually and it can be seen that there is wide range of tumor growth. In Group B, having been treated with HES-DFO alone, a nearly identical range is seen. In Group C, receiving IgG ATRAs alone, tumor regression occurred in 5 out of 12 mice. Two mice show static tumors and 5 showed progression. In Group D, having the combined IgG ATRAs and HES-DFO treatment, 8 of the 11 mice showed no detectable tumor after 6 days of treatment. One mouse had a regressing tumor and two had static tumor growth. Group C and D are significantly different by either simple t-test or Cochran-Cox t-test. It must therefore be concluded that the combined treatment is more efficacious.

The above investigations provide significant evidence of in vitro utility as well as in vivo utility of the present invention. This is further evidenced by the fact that experts knowledgeable in the art of cancer treatment have utilized findings from the above protocols to alter the design of upcoming preclinical trials of IgG ATRAs in primates and the fact that a Phase 1 trial of HES-DFO in cancer patients is also now being planned at the University of Arizona by the same individuals who will be testing IgG ALTRAS in primates. (i.e., IgG ATRA/HES-DFO).

Throughout this application various publications are referenced and are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

REFERENCES/PUBLICATIONS CITED

Cancer Chemother. Rep., Part 3, 3:18–55, 1972.
Chitambar et al., "Effects of different transferrin forms on transferrin receptor expression, iron uptake, and cellular proliferation of human leukemic HL60 cells" J. Clin. Invest. 78:1538-1546, December 1986.
Dillman, "Monoclonal antibodies for treating cancer" Annals of Internal Medicine 111:592–603, 1989.
Estrov et al., "In vitro and In vivo effects of deferoxamine in neonatal acute leukemia" Blood 69:757, 1987.
Foster et al., Cancer Treatment Reports 70:1311-1319, Nov.1986.
Hallaway et al. "Modulation of deferoxamine toxicity and clearance by covalent attachment to biocompatible polymers" Proc. Natl. Acad. Sci. USA 86:10108-10112, 1989.
Harris and Emery, "Therapeutic antibodies—the coming of age" TIBTECH Vol.11, pp.42–44, 1993.
Hird and Epenetos, "Immunotherapy with monoclonal antibodies" in Genes and Cancer, edited by D. Carney and K. Sikera, John Wiley & Sons, Ltd., Chapter 17, 183–89, 1990.
Huse et al., "Generation of a large combinatorial library of the immunoglobulin repertoire in phage lambda" Science 246:1275-1281, 1989.
Kaplinsky et al., "Deferoxamine (Desferal®) induced ocular toxicity" Ped Hemat Oncol 5:293, 1988.
Kemp et al., "Role of the transferrin receptor in lymphocyte growth: A rat IgG monoclonal antibody against the murine transferrin receptor produces highly selective inhibition of T and B cell activation protocols" J Immunol 138:2422, 1987.
Kemp et al., "Inhibition of lymphocyte activation with anti-transferrin receptor Mabs: A comparison of three reagents and further studies of their range of effects and mechanism of action" Cell Immunol 122:218, 1989.
Kemp et al., "Synergistic inhibition of lymphoid tumor growth In Vitro by combined treatment with the iron chelator deferoxamine and an immunoglobulin G monoclonal antibody against the transferrin receptor" Blood, Vol 76, No. 5, pp.991-995, Sep. 1, 1990.
Larrick et al., "In Vitro Expansion of Human B Cells for the Production of Human Monoclonal Antibodies" in Human Hybridomas and Monoclonal Antibodies edited by Engleman and Foung, Plenum Press, NY and London, pp. 149–165, 1985.
Lederman et al., "Deferoxamine: A reversible S-phase inhibitor of human lymphocyte proliferation" Blood 64:748, 1984.
Lesley et al., "Inhibition of cell growth by monoclonal anti-transferrin receptor antibodies" Mol. Cell. Bio. 5:1814, 1985.
Physicians'Desk Reference, 48 Edition, Desferal®, 1994.
Rao et al., "Effects of alterations in cellular iron on biosynthesis of the transferring receptor in K562 cells" Mol. Cell. Biol. 5:595, 1985.
Sauvage et al., "Effects of monoclonal antibodies that block transferrin receptor function on the in vivo growth of a syngeneic murine leukemia" Cancer Res. 47:747, 1987.
Sastry et al., "Cloning of the immunological repertoire in E. coli for generation of monoclonal catalytic antibodies: Construction of a heavy chain variable region-specific cDNA library" Proc. Natl. Acad. Sci. 86:5728-4732, 1989.
Schlom, J. "Monoclonal antibodies: they're more and less than you think" in Molecular Foundations of Oncology, edited by Samuel Broder, Williams & Wilkins, Maryland, Chapter 6, pp.95-134, 1991
Taetle et al, "Mechanisms of growth inhibition by anti-transferrin receptor monoclonal antibodies" Cancer Res. 46:1759-1763, Apr. 1986.
Taetle et al., "Combination iron depletion therapy" J. Natl. Cancer Inst. 81:1229, 1989.
Waldmann, T. "Monclonal antibodies in diagnosis and therapy" Science, Vol. 252, pp.1657–62, June 1991.
Weissman et al., "Exposure of K562 cells to anti-receptor monoclonal antibody OKT9 results in rapid redistribution and enhanced degradation of the transferrin receptor" Journal of Cell Biology, 102:951-958, 1986.

What is claimed is:

1. A method of inhibiting tumor growth, said method including the step of:
depleting intracellular iron levels of tumor cells to increase expression of cellular transferrin receptor in the tumor cells by exposing the tumor cells to deferoxamine and/or derivatives thereof and then exposing the tumor cells to monoclonal IgG anti-transferrin receptor antibody.

* * * * *